United States Patent [19]

Bowman

[11] 4,261,990
[45] Apr. 14, 1981

[54] N-ALKYLENEIMINOALKYL-DICARBOXIMIDES AS ANTIALLERGICS AND ANTIASTHMATICS

[75] Inventor: Robert M. Bowman, Summit, N.J.
[73] Assignee: Ciba-Geigy Corporation, Ardsley, N.Y.
[21] Appl. No.: 18,957
[22] Filed: Mar. 9, 1979

Related U.S. Application Data

[63] Continuation-in-part of Ser. No. 899,149, Apr. 24, 1978, abandoned.

[51] Int. Cl.³ ................. A61K 31/445; C07D 401/06; C07D 403/06; A61K 31/40
[52] U.S. Cl. ............................. 424/244; 260/239.3 R; 260/239.3 B; 260/239.3 T; 260/326.5 FM; 260/326.5 B; 260/326.5 CA; 260/326 N; 260/244.4; 424/265; 424/274; 424/267; 546/16; 546/188; 546/200; 546/208; 546/112; 546/125; 546/126; 546/242; 260/245.7; 546/15; 546/97; 546/183
[58] Field of Search ......... 424/267, 274, 244, 239.3 B, 424/239.3 T, 265; 546/188, 16, 208, 200, 239.3 R, 326 N, 326.5 FM, 326.5 B, 326.5 CA, 15, 183; 260/244.4

[56] References Cited
U.S. PATENT DOCUMENTS 2,833,777  5/1958  Rory ............................. 260/293.71
3,106,552 10/1963  Grogan ......................... 260/293.66
3,171,839  3/1965  Rory ............................. 260/293.71
3,907,801  9/1975  Wu et al. ...................... 260/281
4,042,701  8/1977  Bowman ........................ 424/267

*Primary Examiner*—Mark L. Berch
*Attorney, Agent, or Firm*—Theodore O. Groeger

[57] ABSTRACT

N-(diphenylmethoxy-mono- or bicyclic-alkyleneiminoalkyl)-dicarboximides, e.g. those of the formula

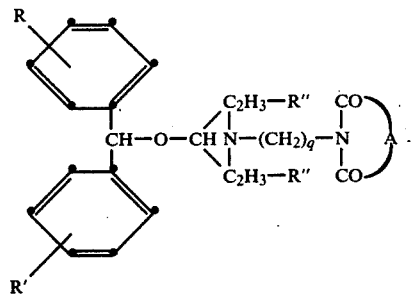

A = aliphatic or cycloaliphatic radical
R,R' = H, alkyl, halogen or CF₃
R" = H or both are ethylene
q = 2-4 and salts thereof are antiallergics and antiasthmatics.

8 Claims, No Drawings

N-ALKYLENEIMINOALKYL-DICARBOXIMIDES AS ANTIALLERGICS AND ANTIASTHMATICS

CROSS-REFERENCE TO RELATED APPLICATION

This is a continuation-in-part of application Ser. No. 899,149, filed Apr. 24, 1978, (now abandoned).

SUMMARY OF THE INVENTION

The present invention concerns and has for its objects the provision of new N-(diphenylmethoxy-mono or bicyclic-alkyleneimino-alkyl)-dicarboximides, more particularly of those of Formula I

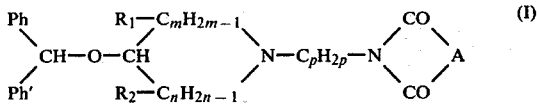

wherein each of Ph and Ph' is phenyl, unsubstituted or monosubstituted by lower alkyl, halogeno or trifluoromethyl; each of $R_1$ and $R_2$ are hydrogen, alkyl with up to 3 carbon atoms, or both $(R_1+R_2)$ together represent alkylene with up to 3 carbon atoms; each of m and n is an integer from 1 to 3; p is an integer from 2 to 7, whereby $C_pH_{2p}$ separates the adjacent nitrogen atoms by at least 2 carbon atoms; and A is lower alkylene, lower alkenylene, lower mono- or bicyclo-alkylene, or -alkenylene, or lower spirocycloalkane-alkylene, unsubstituted or ring-substituted by up to three lower alkyls; or a therapeutically acceptable acid addition salt thereof; of corresponding pharmaceutical compositions and of methods for the preparation and application of these products, which are useful antiasthmatic, antiallergic and antihistaminic agents.

DESCRIPTION OF THE PREFERRED EMBODIMENTS

Of the radicals Ph and Ph' one is preferably phenyl and the other phenyl, (lower alkyl)-phenyl, (halogeno)-phenyl or (trifluoromethyl)-phenyl, wherein alkyl preferably represents methyl, but also ethyl, n- or i-propyl or -butyl; and halogeno is preferably chloro, but also fluoro or bromo.

Each of $R_1$ and $R_2$ is preferably hydrogen, but may also stand for methyl, ethyl or n-propyl; or both $(R_1+R_2)$ are preferably ethylene, but also methylene, 1,2- or 1,3-propylene.

Each of $H-C_mH_{2m-1}$ and $H-C_nH_{2n-1}$ is preferably ethylene, but also, for example, methylene, 1,2- or 1,3-propylene.

The group $C_pH_{2p}$ also represents preferably ethylene, 1,2- or 1,3-propylene or -butylene or 1,4-butylene. The term "lower" referred to above and hereinafter in connection with organic radicals, or compounds, respectively, defines such with up to 7, preferably up to 4, especially with 1 or 2 carbon atoms.

A lower alkylene or alkenylene radical A is preferably ethylene, 1,3-propylene, 2,2-di-(methyl, ethyl, n-propyl or n-butyl)-1,3-propylene, 1,4-butylene or 1,4-but-2-enylene.

A mono- or bicycloalkylene or -alkenylene radical A is preferably 4 to 7 ring-membered and unsubstituted, or ring-substituted by up to 3 lower alkyls, preferably methyls, such as 1,2- or 1,3-cyclopentylene or -cyclohexylene, 1,2,2-trimethyl-1,3-cyclopentylene, 2-methyl-1,3-cyclohexylene, 3,6-ethano-1,2-cyclohexylene or -cyclo-4-hexenylene.

A spirocycloalkane-alkylene radical A is preferably a 4 to 7 ring-membered unsubstituted 2-spirocycloalkane-(ethylene or 1,3-propylene) group, e.g. 2-(spirocylobutane, pentane or hexane)-(ethylene or 1,3-propylene), or such radicals alkylated, preferably methylated, as shown above.

The acid addition salts of the compounds of Formula I are preferably derived from the therapeutically acceptable acids listed below.

The compounds of the invention exhibit valuable pharmacological properties, for example antiasthmatic, antiallergic and antihistaminic effects. This can be demonstrated either in vitro or in vivo tests, using advantageously mammals, such as mice, rats, guinea pigs or dogs as test objects, or isolated organs thereof. The in vitro tests are performed either with human leukocytes of volunteers who are allergic to ragweed pollen, or with the guinea pig ileum in a standard organ bath, e.g. physiological saline. In the former test, as described by Lichtenstein et al., J. Exp. Med. 120, 507 (1964), the aqueous leukocyte suspension, when treated with a purified ragweed pollen extract (antigen E), releases histamine, which can be estimated fluorometrically. The compounds of the invention, especially the N-[2-(4-diphenylmethoxy-piperidino)-ethyl]-$\beta,\beta$-tetramethylene-glutarimide hydrochloride, being illustrative thereof, when added to said ileum bath, in an amount to reach concentrations down to about $10^{-5}$ molar, inhibit the histamine-induced ileum-contraction respectively, thus indicating antiallergic and antihistaminic effects, which latter are also confirmed by the classical in vivo tests in mice, rats and guinea pigs. With enteral or parenteral, e.g. oral or intravenous, doses of said components, for example in the range between 0.1 and 200 mg/kg/day, preferably between about 1 and 100 mg/kg/day; especially with about 5 or 10 mg/kg/day i.v., or with about 50 or 100 mg/kg/day p.o. doses of said hydrochloride, significant protection against eggalbumin anaphylaxis, or passive cutaneous anaphylaxis is achieved (J. Carr, J. Path. 108, 1, 1972).

Antiasthmatic activity is estimated in dogs, which are naturally sensitive to ascaris antigens, causing asthma-like syndromes after inhalation of said nebulized antigens. The compounds of the invention are administered orally or intraveneously in about the same dosage ranges mentioned above, about 30–60 minutes after antigen-challenge, and efficacy is observed by the change in the dogs' respiratory-rate and airway-resistance.

Accordingly, the compounds of the invention can be applied enterally or parenterally, e.g. by inhalation of a nebulized aqueous solution, or by peroral, subcutaneous, intramuscular or intraveneous administration, in about the dosage range shown above. According to the test results obtained, they are useful antiasthmatic, antiallergic and antihistaminic agents. They are also valuable intermediates of other preparations, preferably of pharmacologically useful products.

Particularly useful are compounds of Formula I, wherein each of Ph and Ph' is phenyl, (lower alkyl)-phenyl, (halogen)-phenyl or (trifluoromethyl)-phenyl, each of $R_1$ and $R_2$ are hydrogen, alkyl with up to 3 carbon atoms, or both $(R_1+R_2)$ together represent alkylene with up to 3 carbon atoms; each of m and n is an integer from 1 to 3; p is an integer from 2 to 7, whereby $C_pH_{2p}$ separates the adjacent nitrogen atoms by at least 2 carbon atoms; and A is lower alkylene, lower alkenylene, 4 to 7 ring-membered mono- or bicyclic 1,2- or 1,3-cycloalkylene or -cycloalkenylene, or 4 to 7 ring-membered 2-spirocycloalkane-1,3-propylene, or a therapeutically acceptable acid addition salt thereof.

Preferred compounds of the invention are those of Formula I, wherein each of Ph and Ph' is phenyl, (lower alkyl)-phenyl, (halogeno)-phenyl or (trifluoromethyl)-phenyl; each of $R_1$ and $R_2$ is hydrogen or both ($R_1 + R_2$) together are alkylene with 2 or 3 carbon atoms; each of m and n is the integer 2 or 3; p is an integer from 2 to 4, whereby $C_pH_{2p}$ separates the adjacent nitrogen atoms by at least 2 carbon atoms; and A is straight or branched alkylene or alkenylene with 2-7 carbon atoms, 5 to 7 ring-membered mono- or bicyclic 1,2- or 1,3-cycloalkylene or -cycloalkenylene, or 4 or 7 ring-membered 2-spirocycloalkane-1,3-propylene, or a therapeutically acceptable acid addition salt thereof.

Outstanding on account of their usefulness are the compounds of Formula II

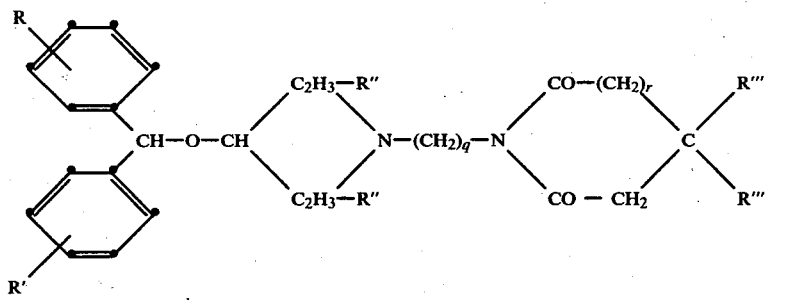

(II)

wherein each of R and R' is hydrogen, alkyl with 1–4 carbon atoms, halogeno or trifluromethyl; each of R" is hydrogen or both R" together represent ethylene; q is 2 to 4, r is 0 or 1 and each of R'" is alkyl with 1–4 carbon atoms, or both R'" together stand for alkylene with 3–5 carbon atoms, or a therapeutically acceptable acid addition salt thereof.

The most preferred compounds are those of Formula II, wherein each of R and R' is hydrogen, methyl or chlorine, each of R" is hydrogen or both R" together are ethylene forming with the bridge heads and the nitrogen atom a 5-membered ring; q is 2 or 3, r is one, and both R'" stand for 1,3-propylene or 1,4-butylene; or a therapeutically acceptable acid addition salt thereof.

The compound of this invention are prepared according to conventional methods, for example, by condensing compounds of formulae III and IV

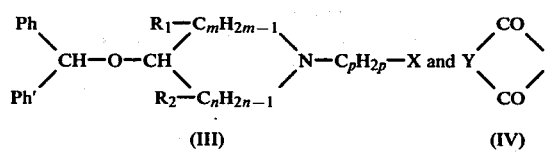

wherein X is amino or reactively esterified hydroxy and Y is oxygen or imino, or alkali metal salts thereof, provided that (X+Y) contain one nitrogen atom only and, if desired, converting any resulting compound of Formula I into another compound of the invention.

A reactively esterified hydroxy group X is preferably a halogen atom, advantageously chloro or bromo, or an aliphatic or aromatic sulfonyloxy group, such as alkane- or Ph-sulfonyloxy, e.g. mesyloxy, besyloxy, tosyloxy, closyloxy or brosyloxy; and an alkali metal salt is preferably the sodium or potassium salt of the compounds with Y=NH.

Said condensation either occurs spontaneously at room temperature or below, or under pyrolytic conditions, for example, at temperatures between room temperature and about 200° and/or in the presence of agents removing the water or acids generated, such as axeotropic solvents, e.g. benzene, toluene or xylene, or alkali metal hydroxides, carbonates or bicarbonates; or tert. amines, e.g. tri-lower alkylamines, pyridine or lower alkylated-pyridines respectively.

In the compounds of Formula I so obtained, any olefinic "A" can be hydrogenated with catalytically activated hydrogen, e.g. hydrogen in the presence of palladium or platinum catalysts.

Any resulting base can be converted into a corresponding acid addition salt, preferably with the use of a therapeutically acceptable acid or anion exchange preparation, or resulting salts can be converted into the corresponding free bases, for example, with the use of a base, such as a metal hydroxide, basic salt, ammonia, amine or cation exchange preparation, e.g. an alkali metal hydroxide or carbonate. Said acid addition salts are preferably such of therapeutically acceptable inorganic or organic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lacetic, malic, tartaric, citric, ascorbic, maleic, hydroxymaleic, pyroracemic, phenylacetic, benzoic, 4-aminobenzoic, anthranilic, 4-hydroxybenzoic, salicyclic, 4-aminosalicylic, pamoic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The starting material of Formulae III and IV are well known diphenylmethoxy-alkyleneimino-alkylamines or -alkanol esters, or dicarboxanhydrides or - imides respectively, described, together with their precursors, inter alia in J. Org. Chem. 37, 3453 (1972) or British Pat. No. 688,354 or Bull. Soc. Chim. France 10, 2572 (1964).

In case mixtures of geometrical or optical isomers of the compounds of Formulae I to IV are obtained, these can be separated into the single isomers by method in themselves known, e.g. by fractional distillation, crystallization and/or chromatography. Racemic products can likewise be resolved into the optical antipodes, for example, by separation of diastereomeric salts thereof, e.g. by the fractional crystallizaton of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Thus, for example, the anhydrides IV may form with the amines III open amides first, which ring-close to the imides I or II by prolonged heating and/or azeotropic water-removal, or the reactive esters III may form intramolecular quaternaries first, e.g. aziridinium salts, which condense in similar fashion. Mainly those starting materials should be used in said reactions that lead to the formation of those compounds indicated above as being especially valuable, e.g. those of Formulae II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable or inhalable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition they may also contain other therapeutically valuable substances. Said compositions are prepared according to conventional mixing, granulating or coating methods respectively and contain about 0.1 to 75%, preferably about 1 to 50%, of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 1 and 100 mm Hg.

EXAMPLE 1

The mixture of 59.5 g of 1-(2-aminoethyl)-4-diphenylmethoxypiperidine, 30.0 g of $\beta,\beta$-tetramethylene-glutaric anhydride and 1,350 ml of xylene is stirred at reflux for 4 hours, during which time the liberated water is removed by a water trap. On cooling, the solution is washed with 2 N aqueous sodium hydroxide and saturated aqueous sodium chloride, dried and evaporated. The residual solid is taken up in acetone, the solution acidified with ethereal hydrogen chloride and the precipitate formed collected, to yield the N-[2-(4-diphenylmethoxypiperidino)-ethyl]-$\beta,\beta$-tetramethylene-glutarimide hydrochloride of the formula

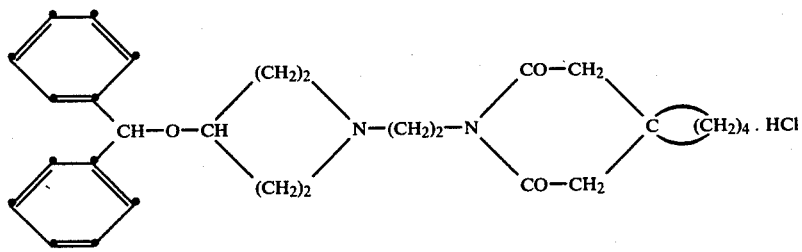

melting at 169°–171°.

The starting material is prepared as follows.

The mixture of 42.0 g of diphenylmethanol, 25.25 g of 4-hydroxypiperidine and 49.4 g of p-toluenesulfonic acid monohydrate is placed in a flask fitted with a thermometer and an air condensor. The reaction vessel is connected to a vacuum pump and heated to 155°–160° until the evolution of water ceases. Upon cooling, the glassy residue is partitioned between 500 ml of diethyl ether and 200 ml of 2 N aqueous sodium hydroxide, the ethereal solution is separated and washed with water and saturated aqueous sodium chloride, dried and evaporated, to yield the 4-diphenylmethoxy-piperidine melting at 56°; (its hydrochloride, prepared in isopropanol-diethyl ether, melts at 175°–177°).

To the solution of 55.0 g of 4-diphenylmethoxy-piperidine in 250 ml of dimethylformamide, 32.0 g of anhydrous potassium carbonate are added while stirring, followed by the dropwise addition of the solution of 17.2 g of chloroacetonitrile in 25 ml of dimethylformamide and the suspension is stirred overnight at room temperature. It is concentrated, partitioned between water and diethyl ether, the organic phase washed with saturated aqueous sodium chloride, dried and evaporated. The residue is recrystallized from ethanol, to yield the 1-cyanomethyl-4-diphenylmethoxypiperidine melting at 78°–80°.

The solution of 61.0 g thereof in 600 ml of diethyl ether is added dropwise to the stirred suspension of 11.4 g of lithium aluminum hydride in 250 ml of anhydrous diethyl ether while cooling with ice. The mixture is stirred at reflux for 6 hours, cooled in an ice-bath and 11.4 ml of water are added dropwise, followed by 11.4 ml of 15% aqueous sodium hydroxide and 34.2 ml of water. The solids are filtered off, washed with diethyl ether, the filtrate dried and evaporated, to give the 1-(2-aminoethyl)-4-diphenylmethoxypiperidine as an oil, its hydrochloride melts at 183°–185°.

EXAMPLE 2

The mixture of 5.95 g of 1-(3-aminopropyl)-3-diphenylmethoxyazetidine, 3.36 g of β,β-tetramethylene-glutaric anhydride and 90 ml of xylene is stirred at reflux for 4 hours, during which time the liberated water is removed by a water trap. On cooling, the solution is washed with 2 N aqueous sodium hydroxide and saturated aqueous sodium chloride, dried and evaporated. The residual solid is taken up in acetone, the solution acidified with ethereal oxalic acid, the precipitate formed collected and recrystallized from acetonitrile to yield the N-[2-(3-diphenylmethoxyazetidino)-propyl]-β,β-tetramethylene-glutarimide oxalate of the formula

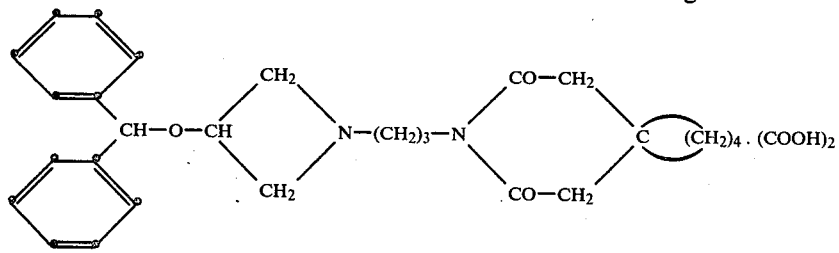

melting at 165°–166°.

The starting material is prepared as follows.

The solution of 10 g of 1-benzhydryl-3-azetidinol in 50 ml of anhydrous dimethylformamide is added dropwise to the stirred, oil-free suspension of 1.05 g of sodium hydride in 20 ml of anhydrous dimethylformamide and the mixture stirred at 45°–50° for 30 minutes. The resulting solution is cooled to room temperature and the solution of 10.6 g of benzhydryl chloride in 50 ml of anhydrous dimethylformamide is added dropwise. The mixture is subsequently stirred at 60° for 18 hours, cooled and poured onto 600 ml of a mixture of crushed ice and water. It is extracted with diethyl ether, the extract washed with water and aqueous sodium chloride, dried and evaporated, to yield the 1-benzhydryl-3-diphenylmethoxyazetidine (the hydrochloride of which melts at 163°–165°).

The solution of the 11.8 g thereof in 100 ml of methylene chloride is treated with 4.75 g of ethyl chloroformate and the solution is refluxed overnight. The solvent is then evaporated and the residue is maintained at 50°/0.5 mm Hg (to remove benzhydryl chloride), to yield the 1-carbethoxy-3-diphenylmethoxyazetidine, useful without further purification. 14.4 g thereof are dissolved in 100 ml of 95% aqueous ethanol and 8.9 g of solid potassium hydroxide are added in portions. The mixture is then stirred and refluxed for 42 hours, cooled and poured onto 300 ml of ice water. It is extracted with diethyl ether, the ethereal solution reextracted with 3 N aqueous hydrochloride acid and the aqueous solution made basic with 50% aqueous sodium hydroxide. It is extracted with diethyl ether, the extract washed with saturated aqueous sodium chloride, dried and evaporated to give the oily 3-diphenylmethoxyazetidine, which is sufficiently pure, to be used directly (its hydrochloride melts at 171°–174°). 6.3 g thereof are dissolved in 30 ml of acrylonitrile and the solution is allowed to stand overnight at room temperature. It is evaporated, leaving the 1-(2-cyanoethyl)-3-diphenylmethoxyazetidine in sufficient purity to be used directly (its oxalate melts at 152°–154°).

The solution of 7.05 g thereof in 60 ml of anhydrous diethyl ether is added dropwise to the ice-cooled and well stirred suspension of 1.39 g of lithium aluminum hydride in 60 ml of anhydrous diethyl ether. Thereafter, the suspension is stirred at reflux for 6 hours, cooled in an ice bath and 1.4 ml of water, 1.4 ml of 15% aqueous sodium hydroxide and 4.2 ml more water are added dropwise. The solids are filtered off, washed with diethyl ether and the filtrate is dried and evaporated, to give the 1-(3-aminopropyl)-3-diphenylmethoxyazetidine as as oil, which is of sufficient purity to be used directly (its dihydrochloride melts at 210°–215°).

According to the analogous method, other compounds of the invention, expecially those of Formula II, are prepared from equivalent amounts of corresponding starting materials.

EXAMPLE 3

0.24 g of an oil dispersion of sodium hydride are washed free of oil with hexane and then suspended in 3 ml of anhydrous dimethylformamide. The solution of 0.84 g of 3,3-tetramethyleneglutarimide in 5 ml of dry dimethylformamide is added dropwise to said suspension at room temperature and the mixture is stirred for additional 30 minutes before the solution of 0.92 of 1-(2-chloroethyl)-4-diphenylmethoxypiperidine hydrochloride in 5 ml of dry dimethylformamide is added dropwise. After stirring the mixture at room temperature for 18 hours, it is poured onto 30 ml of ice water and repeatedly extracted with diethyl ether. The extract is washed successively with 1 N aqueous sodium hydroxide and brine, dried and evaporated. The residue is taken up in ethyl acetate and the solution acidified with ethereal hydrogen chloride, to yield the N-[2-(4-diphenylmethoxypiperidino)-ethyl]-β,β-tetramethyleneglutarimide hydrochloride, melting at 169°–171°; it is identical with the compound obtained according to Example 1. Analogously the other compounds of the previous examples can be prepared.

The starting material is obtained as follows. The solution of 13.35 g of 4-diphenylmethoxypiperidine in 40 ml of methanol, containing 3.52 g of ethylene oxide and 0.9 ml of water, is stirred and heated in an oil bath at 42°–44° for 4 hours. The bath temperature is raised to 50° and heating and stirring are continued for an additional 3 hours. The solution is then evaporated and the residue taken up in 1 N hydrochloric acid and washed with diethyl ether. The aqueous solution is made basic with 50% aqueous sodium hydroxide and repeatedly extracted with diethyl ether. The extract is washed with brine, dried and evaporated to give the 1-(2-hydroxyethyl)-4-diphenylmethoxypiperidine, melting at 83°–85° after recrystallization from cyclohexane.

The solution of 3.11 g thereof in 10 ml of benzene is treated with 10 ml of thionyl chloride and the solution is refluxed for 2 hours. It is concentrated and the solvent replaced by 20 ml of fresh benzene and again concentrated, which process is repeated twice. The residue is triturated with ethyl acetate, filtered off and recrystallized from isopropanol-diethyl ether to yield the 1-(2-chloroethyl)-4-diphenylmethoxypiperidine hydrochloride, melting at 169°–171°.

EXAMPLE 4

1.15 g of 3,3-tetramethyleneglutaric anhydride are added all at once to the solution of 2.22 g of 3-diphenylmethoxy-8-azabicyclo[3.2.1]octane in 40 ml of xylene and the mixture is refluxed for 5 hours while liberated water is removed by a trap. The resulting solution is cooled, washed successively with 2 N aqueous sodium hydroxide, water and brine, dried and evaporated. The residue is dissolved in ethyl acetate and the solution acidified with ethereal hydrogen chloride, to yield the N-[2-(3-diphenylmethoxy-8-azabicyclo[3.2.1]octyl)-ethyl]-β,β-tetramethyleneglutarimide hydrochloride of the formula

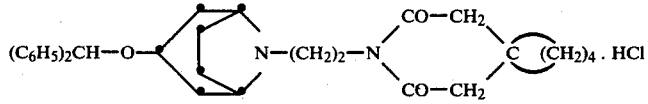

melting at 240°–243° with decomposition.

The starting material is prepared as follows. The intimate mixture of 9.20 g of benzhydrol 7.05 g of tropine and 10 g of p-toluenesulfonic acid monohydrate is placed in a flask which is fitted with an air condensor and a vacuum take-off. The flask is evacuated and maintained in vacuo while being heated in an oil bath to 165°–170°, whereby the liberated water is removed. After 2 hours, the mixture is cooled and partitioned between 100 ml of water and diethyl ether each. The aqueous solution is separated, washed once more with diethyl ether and made basic with 50% aqueous sodium hydroxide. It is extracted repeatedly with diethyl ether, the extract washed with brine and evaporated to give 3-diphenylmethoxy-8-methyl-8-azabicyclo[3.2.1]octane, which is sufficiently pure to be used in the next step.

The solution of 6.60 g thereof in 400 ml of pyridine is mixed with the solution 7.50 g of potassium permanganate in 400 ml of water and the whole is stirred at room temperature for 18 hours. The mixture is filtered, the filtrate is concentrated, and the residual oil is dissolved in diluted hydrochloric acid. The solution is washed with diethyl ether and made basic with 50% aqueous sodium hydroxide. The basic solution is extracted repeatedly with diethyl ether, the extract dried and evaporated, to yield the 3-diphenylmethoxy-8-azabicyclo[3.2.1]octane (its hydrochloride melts at 240°–242°).

The solution of 2.60 g thereof in 10 ml of anhydrous dimethylformamide, containing 1.38 g of anhydrous potassium carbonate, is stirred at room temperature during the dropwise addition of the solution of 0.75 g of chloroacetonitrile in 5 ml of dimethylformamide. The mixture is stirred at room temperature for 18 hours and then diluted with 50 ml of ice water. It is extracted repeatedly with diethyl ether, the extract washed with brine, dried and evaporated, to yield the 3-diphenylmethoxy-8-cyanomethyl-8-azabicyclo[3.2.1]octane, melting at 94°–97°.

The solution of 2.20 g thereof in 35 ml of anhydrous diethyl ether is added dropwise to the stirred, and ice-cooled suspension of 0.42 g of lithium aluminum hydride in 10 ml of diethyl ether. The mixture is subsequently stirred at room temperature for 18 hours and again cooled in an ice bath. It is treated successively by dropwise addition of 0.42 ml of water, 0.42 ml of 15% aqueous sodium hydroxide and 1.26 ml of water. The suspension is filtered, dried and evaporated, to yield the 3-diphenylmethoxy-8-(2-aminoethyl)-8-azabicyclo[3.2.1]octane, which is sufficiently pure for further consumption.

EXAMPLE 5

The mixture of 9.1 g of 1-(2-aminoethyl)-3-diphenylmethoxypiperidine, 5.05 g of β,β-tetramethylene-glutaric anhydride and 110 ml of xylene is stirred at reflux for 4½ hours on a water trap. After cooling, the solution is washed with 2 N aqueous sodium hydroxide and saturated aqueous sodium chloride, dried and evaporated. The residue is taken up in the minimum amount of ethyl acetate and the solution acidified with ethereal hydrogen chloride, to yield the N-[2-(3-diphenylmethoxypiperidino)ethyl]-β,β-tetramethyleneglutarimide hydrochloride hemihydrate, melting at 125°–135° after recrystallization from isopropanol.

The starting material is prepared as follows. The mixture of 8.28 g of diphenylmethanol, 5.05 g of 3-hydroxypiperidine and 9.5 g of p-toluene sulfonic acid monohydrate is heated to 160°–165° while evacuating the evolving water rapidly. After the water emission ceases, the mixture is heated to said temperature for 3 hours. It is allowed to cool to room temperature and is partitioned between 2 N aqueous sodium hydroxide and diethyl ether. The organic solution is separated, washed with water and saturated aqueous sodium chloride, dried and evaporated. The residue is taken up in diethyl ether, the solution extracted with 0.1 N hydrochloric acid, the extract washed with diethyl ether and made basic with saturated aqueous ammonia. It is re-extracted with diethyl ether, the extract dried and evaporated, to yield the 3-diphenylmethoxypiperidine as an oil.

To the solution of 8.2 g thereof in 40 ml of dimethylformamide, 2.6 g of chloroacetonitrile and 5.5 g of anhydrous potassium carbonate are added and the mixture is stirred at room temperature for 38 hours. It is poured into 120 ml of ice water, the mixture extracted with diethyl ether, the extract washed with water and saturated aqueous sodium chloride, dried and evaporated, to yield the 1-cyanomethyl-3-diphenylmethoxypiperidine, melting at 97°–99°.

The solution of 9.6 g thereof in 120 ml of diethyl ether is added dropwise to the stirred suspension of 1.7 g of lithium alminumhydride in 50 ml of anhydrous diethyl ether while cooling with ice. The mixture is refluxed for 6 hours and allowed to stand overnight. It is combined with 1.7 ml of water, 1.7 ml of 15% aqueous sodium hydroxide and 5.1 ml of water, the solids are filtered off, washed with diethyl ether and the filtrate is dried and evaporated, to yield the 1-(2-aminoethyl)-3-diphenyl-methoxypiperidine as an oil; its dihydrochloride melts at 221°–223° after recrystallization from isopropanol.

EXAMPLE 6

The mixture of 772 g of 1-(2-aminoethyl)-4-diphenyl-methoxypiperidine, 416 g of $\beta,\beta$-tetramethylene-glutaric anhydride and 15,800 ml of xylene is stirred at reflux for 6.5 hours, during which time the liberated water is removed by a water trap. After cooling, the solution is washed with 2N aqueous sodium hydroxide and saturated aqueous sodium chloride, dried and evaporated at 60°. The residual solids is taken up in 2,000 ml of ethanol at 70°, the solution filtered hot and the filtrate allowed to cool overnight in the icebox. The precipitate formed is collected and dried at 40°, to yield the N-[2-(4-diphenylmethoxypiperidino)ethyl]-$\beta,\beta$-tetramethylene-glutarimide melting at 108°–110°.

885 g thereof are dissolved in 2,250 ml of hot ethanol, the solution is allowed to cool to 50° and 300 ml of 6.5 N ethanolic hydrochloric acid are rapidly added while stirring. The precipitate formed is filtered off, washed with ethanol and dried at 60°. 840 g thereof are again dissolved in 2,150 ml of ethanol at 80° and the solution allowed to cool to room temperature while stirring for 4 hours. The resulting suspension is filtered, the residue again recrystallized from 2,150 ml of ethanol and dried at 60°, to yield the corresponding hydrochloride melting at 176°–178°; it is somewhat purer than that obtained according to Example 1.

The starting material is prepared as follows: The mixture 268 of diphenylmethanol, 200 g of 4-hydroxypiperidine hydrochloride and 28.8 g of p-toulenesulfonic acid monohydrate is stirred and heated to 160° while reducing the pressure to 0.2 mm Hg with a vacuum pump for 3 hours. It is cooled to 80°, dissolved in 500 ml of ethanol and the solution cooled to 10°. The resulting suspension is filtered, the residue washed with isopropanol and dried at 60°, to yield the 4-diphenylmethoxy-piperidine hydrochloride. It is suspended in 1,800 ml of water, converted into the free base with 125 ml of aqueous ammonia and extracted with diethyl ether and the extract evaporated.

To the solution of 578 g thereof in 5,700 ml of benzene, 360 g of anhydrous potassium carbonate are added while stirring, followed by 207 g of chloroacetonitrile and the suspension is stirred uder nitrogen at room temperature for 72 hours. It is filtered and the filtrate evaporated, to yield the 1-cyanomethyl-4-diphenylmethoxy-piperidine.

The solution of 802 g thereof in 10,000 ml of tetrahydrofuran is added during 90 minutes to the stirred suspension of 150 g of lithium aluminumhydride in 10,000 ml of tetrahydrofuran while cooling to 10°. The mixture is stirred for 1 hour at room temperature, for 6 hours at reflux and overnight at room temperature. It is cooled to 5° and 150 ml of water are added dropwise, followed by 600 ml of 1.2 N aqueous sodium hydroxide at 0°–5°. The solids are filtered off, washed with tetrahydrofuran, the filtrate dried and evaporated, to give the 1-(2-aminoethyl)-4-diphenylmethoxypiperidine.

EXAMPLE 7

According to the methods illustrated by the previous examples, the following compounds of Formula II are prepared from equivalent amounts of the corresponding starting materials: $C_2H_3R''=(CH_2)_2$; B=boiling point at 0.5 mm Hg.

| No. | R | R' | q | r | R''' | R''' | Salt | m.p. °C. |
|---|---|---|---|---|---|---|---|---|
| 1 | H | H | 3 | 1 | $CH_3$ | $CH_3$ | HCl | 195–197 |
| 2 | H | H | 2 | 1 | $C_2H_5$ | $C_2H_5$ | HCl | 164–170 |
| 3 | H | H | 3 | 1 | $(CH_2)_4$ | | HCl | 176–179 |
| 4 | H | H | 4 | 1 | $(CH_2)_4$ | | HCl | 177–179 |
| 5 | 2-$CH_3$ | H | 2 | 1 | $(CH_2)_4$ | | HCl½$H_2O$ | 164–167 |
| 6 | 2-Cl | H | 2 | 1 | $(CH_2)_4$ | | HCl½$H_2O$ | 120 |
| 7 | 4-Cl | 4-Cl | 2 | 1 | $(CH_2)_4$ | | — | 165–167 |
| 8 | 3-$CF_3$ | H | 2 | 1 | $(CH_2)_4$ | | — | B 180–190 |
| 9 | H | H | 2 | 0 | $(CH_2)_4$ | | oxalate | 144–147 |
| 10 | H | H | 2 | 1 | $(CH_2)_5$ | | HCl | 168–169 |
| 11 | H | H | 2 | 1 | $(CH_2)_3$ | | HCl | 166–168 | i.e the hydrochlorides (or oxalate-hemihydrate) of the: (1) N-[3-(4-diphenylmethoxypiperidino)-propyl]-$\beta,\beta$-dimethylglutarimide or (2) -ethyl]-$\beta,\beta$-diethylglutarimide; (3) N-[4-(4-diphenylmethoxypiperidino)-propyl] mide; or (4) -butyl]- or (5) N-[2-[4-($\alpha$-phenyl-o-methylbenzyloxy)-piperidino]-ethyl- or (6) N-[2-(4-$\alpha$-phenyl-o-chlorobenzyloxy-piperidino)-ethyl]- or (7) N-[2-(4di-p-chlorophenylmethoxypiperidino)-ethyl]- or (8) N-[2-(4-$\alpha$-phenyl-m-trifluoromethylbenzyloxy)-piperidino] $\beta,\beta$-tetramethyleneglutarimide; (9) N-[2-(4-diphenylmethoxypiperidino)-ethyl]-$\alpha,\alpha$-tetramethylenesuccinimide; (10) -$\beta,\beta$-pentamethyleneglutarimide or (11) -$\beta,\beta$-trimethyleneglutarimide.

The starting material for said product No. (4) is prepared as follows. The mixture of 4.63 g of 4-diphenyl-methoxypiperidine, 4.63 g of anhydrous sodium carbonate, 0.3 g of sodium iodide, 1.81 g of 4-chlorobutyronitrile and 60 ml of 4-methyl-2-pentanone is stirred and refluxed for 22 hours. It is evaporated, the residue taken up in diethyl ether, the solution washed with 2N aqueous sodium hydroxide and saturated aqueous sodium chloride, dried and evaporated, to give the 1-(3-cyanopropyl)-4-diphenylmethoxypiperidine, which is sufficiently pure to be used directly for the reduction to the 1-(4-aminobutyl)-4-diphenylmethoxypiperidine previously described.

The dihydrochlorides of said compounds of Formula III with X=$NH_2$ melt as follows: (3) 211°–213°; (4) 174°–177°; (7) 232°–234° and the hydrochloride for (6) melts at 153°–155°.

The starting materials may also be prepared according to the following method, e.g. those for products Nos. 5 and 9. The solution of 45.8 g of sodium bisulfite in 110 ml of water is added to 37 ml of aqueous 37% formaldehyde while stirring. After 45 minutes it is mixed with the solution of 40.5 g of 4-hydroxypiperidine in 65 ml of water and the resulting solution is stirred at room temperature for 2.5 hours, whereupon the solution of 28.7 g of potassium cyanide in 80 ml of water is rapidly added. The mixture is stirred at room temperature for further 2.5 hours, whereupon 54 g of potassium carbonate are added. It is extracted with chloroform, the extract is washed with brine, dried and evaporated, to afford the (4-hydroxypiperidiono)- acetonitrile melting at 75°–77°; it is used without further purification.

The solution of 6.3 g thereof and 10.8 g of α-phenyl-o-methylbenzyl chloride in 25 g of N-methyl-morpholine is stirred at reflux for 12 hours. Upon cooling, the mixture is diluted with 50 ml of toluene and filtered. The filtrate is washed with water, dried, evaporated, the residue distilled and the fraction boiling at 140°–150°/0.2 mm Hg collected, to yield the [4-(α-phenyl-o-methylbenzyloxy)-piperidino]-acetonitrile.

The solution of 10.0 thereof in 100 ml of tetrahydrofuran is added dropwise to the solution of 1.98 g of alane, prepared by cautiously adding dropwise 1.92 g of 96% sulfuric acid to the suspension of 2.5 of lithium tetrahydroaluminate in 100 ml of tetrahydrofuran while stirring and cooling to 0°. The resulting suspension is stirred at ambient temperature for 18 hours, again cooled to 0° and cautiously treated with 22.5 ml of 15% aqueous sodium hydroxide. The mixture is filtered, the filtrate dried and evaporated, to afford the 1-(2-aminoethyl)-4-(α-phenyl-o-methylbenzyloxy)-piperidine, which can be used directly without purification. Its hydrated dihydrochloride melts at 116°–119°.

The α,α-tetramethylenesuccinic acid is prepared according to LeMoal et al, Bull. Soc. Chim. France 579 (1964) and 27.0 g thereof are dissolved in 130 ml of acetic anhydride. The solution is refluxed for 6 hours and acetic acid and excess acetic anhydride are evaporated. The residual anhydride is distilled and the fraction boiling at 75°–85°/0.5 mm Hg collected.

EXAMPLE 8

Preparation of 10,000 tablets each containing 50.0 mg of the active ingredient:

Formula

| | |
|---|---|
| N-[2-(4-diphenylmethoxypiperidino)-ethyl]-β,β-tetramethylene-glutarimide hydrochloride | 500.00 g |
| Lactose | 1,706.00 g |
| Polyethylene glycol 6,000 | 90.000 g |
| Talcum powder | 90.00 g |
| Magnesium stearate | 24.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Analogously tablets of said other compounds of the invention are prepared, preferably of those corresponding to Formula II and being illustrated by the previous examples.

EXAMPLE 9

Upon mixing 3.1 g of 1-(2-aminoethyl)-4-diphenylmethoxypiperidine and 1.26 g of cis-1,2-cyclobutanedicarboxylic anhydride in 40 ml of xylene at room temperature, a precipitate separates almost immediately. The suspension is stirred and refluxed for 5 hours, when the solid dissolves and the liberated water is removed by a water trap. Upon cooling the solution is decanted from a small amount of insoluble gum and then evaporated, to yield the N-[2-(4-diphenylmethoxypiperidino)-ethyl]-cis-1,2-cyclobutanedicarboximide melting at 55°–58°. It is taken up in the minimum amount of acetone, the solution acidified with oxalic acid and the precipitate collected, to yield the corresponding oxalate melting at 146°–148°.

In a similar manner the following oxalates are obtained from equivalent amounts of the corresponding other acid anhydrides:
(1) N-[2-(4-diphenylmethoxypiperidino)-ethyl]-1,2,3,6-tetrahydrophthalimide melting at 104°–106°;
(2) N-[2-(4-diphenylmethoxypiperidino)-ethyl]-trans-hexahydrophthalimide melting at 148°–151° and
(3) N-[2-(4-diphenylmethoxypiperidino)-ethyl]-endo-bicyclo[2,2,2]octa-5-ene-2,3-dicarboximide melting at 163°–164°.

I claim:
1. A compound of the formula

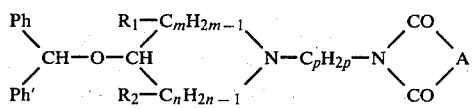

wherein each of Ph and Ph' is phenyl, unsubstituted or monosubstituted by lower alkyl, halogeno or trifluoromethyl; each of $R_1$ and $R_2$ are hydrogen, alkyl with up to 3 carbon atoms, or both $(R_1+R_2)$ together represent alkylene with up to 3 carbon atoms; each of m and n is an integer from 1 to 3; p is an integer from 2 to 7, whereby $C_pH_{2p}$ separates the adjacent nitrogen atoms by at least 2 carbon atoms; and A is alkylene or alkenylene with 2–7 carbon atoms, 4 to 7 ring-membered mono- or bicyclo-alkylene or -alkenylene, or 4 to 7 ring-membered 2-spiro-cycloalkane- (ethylene or 1,3-propylene) unsubstituted or ring-substituted by up to three lower alkyls, or a therapeutically acceptable acid addition salt thereof.

2. A compound as claimed in claim 1, in which formula each of Ph and Ph' is phenyl, (lower alkyl)-phenyl, (halogen)-phenyl or (trifluoromethyl)-phenyl, each of $R_1$ and $R_2$ are hydrogen, alkyl with up to 3 carbon atoms, or both $(R_1+R_2)$ together represent alkylene with up to 3 carbon atoms; each of m and n is an integer from 1 to 3; p is an integer from 2 to 7, whereby $C_pH_{2p}$ separates the adjacent nitrogen atoms by at least 2 carbon atoms; and A is alkylene or alkenylene with 2–7 carbon atoms, 4 to 7 ring-membered mono- or bicyclic 1,2- or 1,3-cycloalkylene or -cyclo-alkenylene, or 4 to 7 ring-membered 2-spirocycloalkane-1,3-propylene, or a therapeutically acceptable acid addition salt thereof.

3. A compound as claimed in claim 1, in which formula each of Ph and Ph' is phenyl, (lower alkyl)-phenyl, (halogeno)-phenyl or (trifluoromethyl)-phenyl; each of $R_1$ and $R_2$ is hydrogen or both $(R_1+R_2)$ together are alkylene with 2 or 3 carbon atoms; each of m and n is the integer 2 or 3; p is an integer from 2 to 4, whereby $C_pH_{2p}$ separates the adjacent nitrogen atoms by at least 2 carbon atoms; and A is straight or branched alkylene or alkenylene with 2–7 carbon atoms, 4 to 7 ring-membered mono- or bicyclic 1,2- or 1,3-cycloalkylene or -chcloalkeneylene, or 4 to 7 ring-membered 2-spirocycloalkane-1,3-propylene, or a therapeutically acceptable acid addition salt thereof.

4. A compound as claimed in claim 1 and corresponding to the formula

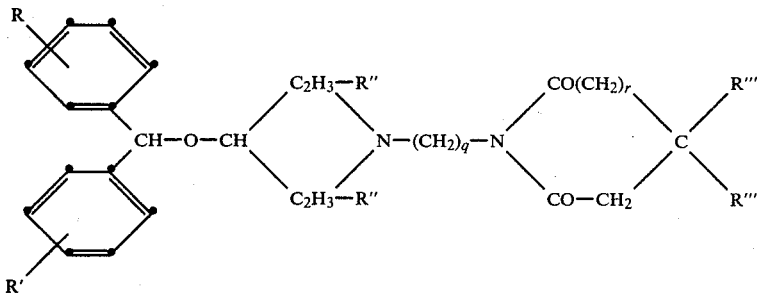

wherein each of R and R' is hydrogen, alkyl with 1-4 carbon atoms, halogeno or trifluoromethyl; each of R" is hydrogen or both R" together represent ethylene; q is 2 to 4, r is 0 or 1 and each of R''', is alkyl with 1-4 carbon atoms, or both R''' together stand for alkylene with 3-5 carbon atoms, or a therapeutically acceptable acid addition salt thereof.

5. A compound as claimed in claim 4, in which formula each of R and R' is hydrogen, methyl or chlorine, each of R" is hydrogen or both R" together are ethylene forming with the bridge heads and the nitrogen atom a 5-membered ring; q is 2 or 3 r is one and both R''' stand for 1,3-propylene or 1,4-butylene; or a therapeutically acceptable acid addition salt thereof.

6. A compound as claimed in claim 4 and being the N-[2-(4-diphenylmethoxy-piperidino)-ethyl]-$\beta,\beta$-tetramethylene-glutarimide, or a therapeutically acceptable acid addition salt thereof.

7. An antiallergic and antiasthmatic pharmaceutical composition consisting essentially of a correspondingly effective amount of a compound claimed in claim 1, together with a pharmaceutical excipient.

8. A method of treating allergic and asthmatic conditions in mammals, which consists in administering to said mammals enterally or parenterally a composition as claimed in claim 7.

* * * * *